(12) United States Patent
Croizat et al.

(10) Patent No.: US 8,926,574 B2
(45) Date of Patent: Jan. 6, 2015

(54) WOUND DRESSING FOR NEGATIVE-PRESSURE THERAPY

(75) Inventors: Pierre Croizat, Herbrechtingen (DE);
Axel Eckstein, Heidenheim (DE);
Ulrich Fink, Heidenheim (DE); Jürgen Hofstetter, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 13/301,993

(22) Filed: Nov. 22, 2011

(65) Prior Publication Data

US 2012/0136326 A1 May 31, 2012

Related U.S. Application Data

(60) Provisional application No. 61/417,983, filed on Nov. 30, 2010.

(30) Foreign Application Priority Data

Nov. 25, 2010 (DE) .......................... 10 2010 052 336

(51) Int. Cl.
| | | |
|---|---|---|
| *A61M 1/00* | (2006.01) | |
| *A61F 13/02* | (2006.01) | |
| *A61F 13/00* | (2006.01) | |
| *A61F 13/14* | (2006.01) | |

(52) U.S. Cl.
CPC ......... *A61F 13/022* (2013.01); *A61F 13/00017* (2013.01); *A61F 13/00068* (2013.01); *A61F 13/00987* (2013.01); *A61M 1/0088* (2013.01); *A61F 13/148* (2013.01); *A61F 13/14* (2013.01); *A61F 2013/00174* (2013.01); *A61F 2013/00536* (2013.01); *A61F 2013/0054* (2013.01); *A61F 2013/00544* (2013.01); *A61F 2013/00855* (2013.01)
USPC .............................. 604/313; 604/319; 602/47

(58) Field of Classification Search
USPC ................ 604/313, 319, 543; 602/41, 46, 47, 602/52–55
See application file for complete search history.

(56) References Cited

U.S. PATENT DOCUMENTS

| | | | |
|---|---|---|---|
| 5,636,643 A | 6/1997 | Argenta et al. | |
| 5,645,081 A | 7/1997 | Argenta et al. | |
| 7,381,859 B2 | 6/2008 | Hunt et al. | |
| 2004/0243073 A1* | 12/2004 | Lockwood et al. | 604/313 |
| 2005/0070858 A1 | 3/2005 | Lockwood et al. | |
| 2006/0025727 A1* | 2/2006 | Boehringer et al. | 604/313 |
| 2006/0041247 A1 | 2/2006 | Petrosenko et al. | |
| 2007/0293830 A1* | 12/2007 | Martin | 604/289 |
| 2008/0243044 A1 | 10/2008 | Hunt et al. | |
| 2008/0249485 A1* | 10/2008 | Effing | 604/304 |
| 2008/0283064 A1* | 11/2008 | Block et al. | 128/853 |

(Continued)

FOREIGN PATENT DOCUMENTS

| | | |
|---|---|---|
| GB | 2423019 A | 8/2006 |
| WO | WO 93/09727 A1 | 5/1993 |

(Continued)

*Primary Examiner* — Melanie Hand
(74) *Attorney, Agent, or Firm* — Dilworth & Barrese, LLP (57) ABSTRACT

The present invention relates to a bandage for use in negative-pressure wound therapy, more particularly for wounds in the abdominal region, comprising a flexible film as a wound contact layer and at least one conduit applied to the film, wherein the conduit communicates with the wound space through openings in the conduit and in the film.

20 Claims, 3 Drawing Sheets

(56) References Cited

U.S. PATENT DOCUMENTS

| | | |
|---|---|---|
| 2009/0099519 A1 | 4/2009 | Kaplan |
| 2009/0216170 A1* | 8/2009 | Robinson et al. ............... 602/60 |
| 2011/0040268 A1 | 2/2011 | Eckstein et al. |
| 2011/0040288 A1 | 2/2011 | Eckstein et al. |
| 2011/0060204 A1* | 3/2011 | Weston ........................ 600/364 |
| 2011/0152800 A1 | 6/2011 | Eckstein et al. |
| 2011/0184361 A1 | 7/2011 | Crojzat et al. |
| 2011/0184362 A1 | 7/2011 | Croizat et al. |
| 2011/0224635 A1 | 9/2011 | Hunt et al. |
| 2012/0046588 A1 | 2/2012 | Eckstein et al. |

FOREIGN PATENT DOCUMENTS

| | | |
|---|---|---|
| WO | WO 01/85248 A1 | 11/2001 |
| WO | WO 02/43634 A2 | 6/2002 |
| WO | 03/057307 A1 | 7/2003 |
| WO | WO 03/057071 A2 | 7/2003 |
| WO | WO 03/086232 A2 | 10/2003 |
| WO | WO 2004/018020 A1 | 3/2004 |
| WO | WO 2007/123451 A1 | 11/2007 |
| WO | WO 2008/131895 A1 | 11/2008 |
| WO | WO 2009/142598 A1 | 11/2009 |
| WO | WO 2010/033272 A1 | 3/2010 |
| WO | 2010/051067 A1 | 5/2010 |
| WO | 2010/051070 A1 | 5/2010 |
| WO | 2010/051071 A1 | 5/2010 |
| WO | 2010/051072 A1 | 5/2010 |
| WO | WO 2010/051068 A1 | 5/2010 |
| WO | WO 2010/051073 A1 | 5/2010 |
| WO | WO 2010051073 A1 * | 5/2010 |
| WO | 2010/072309 A1 | 7/2010 |
| WO | 2010/075180 A1 | 7/2010 |
| WO | 2011/076340 A1 | 6/2011 |

\* cited by examiner

WOUND DRESSING FOR NEGATIVE-PRESSURE THERAPY

CROSS REFERENCE TO RELATED APPLICATIONS

The present application claims priority to U.S. provisional application Ser. No. 61/417,983 filed Nov. 30, 2010, which is herein incorporated by reference in its entirety.

BACKGROUND

The present invention relates to a dressing for use in negative-pressure wound therapy, more particularly for wounds in the abdominal region, comprising a flexible film as a wound contact layer and at least one conduit applied to the film, wherein there can be a fluid-conducting connection between the conduit and the wound space through openings in the conduit and in the film.

Apparatus for negative-pressure wound therapy are known in the prior art. For instance, WO 1993/009727 describes an apparatus for promoting wound healing by the application of negative pressure on the area of skin including the wound and surrounding the wound. The apparatus according to WO 1993/009727 comprises vacuum means for creating the negative pressure, an air-tight wound covering referred to as sealing means, which is operatively associated with the vacuum means, and a wound dressing referred to as screen means for positioning on the wound within the sealing means. The screen means is a porous polymer foam material, for example a polyester foam. According to the description of WO 1993/009727, the use of negative-pressure therapy can speed up wound healing of different types of wounds, such as, for example, burn wounds, pressure sores or lacerations.

Large-area wounds in particular can occur in the abdominal region either as a result of injuries or as a result of surgical procedures. Surgical procedures in the abdominal region are, for example, performed in the surgical treatment of acute and life-threatening diseases of the abdominal cavity. In the context of postoperative care of such surgical procedures, there may also be the need to cover only temporarily the open abdominal region by means of a temporary covering.

WO 01/85248 discloses a dressing for the temporary covering of wounds resulting from accidents or surgical procedures, more particularly abdominal wounds. The dressing is intended for use in negative-pressure therapy. WO 01/85248 proposes covering the floor of the wound with a film provided with holes. A porous foam is applied to the film, which represents the wound contact layer. On the side facing away from the wound, the dressing comprises a liquid-impermeable film drape having an adhesive edge for air-tight closure of the wound area. In addition, connection means are provided, which extend through the film drape up to the porous foam, so that the wound space can be connected with a negative-pressure source. During operation, wound exudate can be removed from the wound space, with the liquid reaching, through the openings of the perforated film, first the porous foam and further on, via the foam, the connection means, which is in direct contact with the porous foam.

WO 01/85248 aims in particular for a temporary wound closure which can be changed without injuries owing to covering the floor of the wound with the dressing. Injuries during change of dressing are avoided according to WO 01/85248 by reducing the direct contact of porous material with the floor of the wound.

According to one embodiment of WO 01/85248, the dressing comprises one or more further layers of porous foam material, wherein the foam layer on the wound side is surrounded on all sides by the film provided with holes.

An abdominal wound dressing having a structure according to WO 01/85248 is commercially available under the name V.A.C.® "Abdominal™ Dressing Kit" (KCI).

Foam layers surrounded by a closed envelope cannot be cut to the size of the wound, since the envelope would otherwise be destroyed.

US 2009/0099519 describes an abdominal dressing for negative-pressure therapy, comprising a heating element for temperature control. In addition, the dressing can likewise comprise a foam layer (pad) surrounded by a closed envelope, wherein the thus encapsulated foam layer can be in direct contact with the wound.

A foam layer applied to the wound contact layer, as described in WO01/85248 for example, is, when using the apparatus as a temporary wound closure, in direct contact with the wound edges, since these are not sutured or closed during the duration of the temporary opening. The contact between foam layer and wound edges has an advantageous effect on the growth of the wound edges and therefore facilitates the primary wound closure when the wound is finally closed after it has been kept open temporarily.

However, in the case of an apparatus as described in WO 01/85248, i.e., in the case of an abdominal wound dressing comprising not only a film provided with holes as a wound contact layer but also a foam layer, any contact between the foam layer and the floor of the wound (i.e., exposed organs or omentum majus) must be avoided as far as possible in order to avoid the foam and the exposed organs or omentum majus sticking together or growing together. Contact between the foam layer and the floor of the wound through the openings of the film must therefore likewise be avoided. The wound contact layer applied between the porous foam and the floor of the wound therefore ought to have, according to WO 01/85248, openings which constitute less than 10% of the area of the film, more particularly only 1-2% of the area or less. According to WO 01/85248, the openings in the film can also be present in the form of slits, which further reduces contact between the foam and the floor of the wound.

However, a reduction in the area of the openings in the film serving as a wound contact layer can lead to reduced permeability to wound fluid, and so the removal of exudate from the wound space to the foam layer might be impeded.

During the duration of application of an abdominal wound dressing, more particularly when using an abdominal wound dressing as a temporary wound closure, it may be necessary to drain a very large amount of liquid, for example more than 5 liters within 48 hours. There may be very large amounts of liquid to be drained during, for example, the surgical treatment of an intestinal obstruction (ileus) or a peritoneal inflammation (peritonitis). In the case of the abdominal wound dressings known from the prior art, comprising a combination of a film provided with holes and a foam layer, the open area of the openings may, as described above, be limiting for the removal of the exudate. Furthermore, the fluid permeability of the foam layer may also be limiting for the removal of the exudate: the fluid permeability of the foam layer may be reduced owing to compression which occurs during application of negative pressure and which leads to a reduction in the pore volumes of the foam. In addition, during the duration of use, the fluid conductibility of the foam may be further impaired by clumping caused by exudate constituents.

In the case of abdominal wound dressings which are currently commercially available, the foam layer is typically smaller than the film provided with openings, and so although the foam layer covers the central surface area of the film, it does not cover the edge area of the film. Typically, the foam layer, provided it is a foam layer which can be adjusted in size, is adjusted in shape to the wound edges, and so the foam layer is in contact with the wound edges, while an edge area of the film provided with openings is carefully inserted between the inner organs and the abdominal wall. When inserting the film provided with openings between the inner organs and the abdominal wall, this must be done very carefully so as not to injure the inner organs. Since no cavity is present in the space formed by the inner organs and the abdominal wall, fluid cannot be removed via the edge area of the film provided with openings inserted under the abdominal wall. For the draining of wound exudate, therefore, only the foam layer-covered area of the film provided with openings is available.

SUMMARY OF THE INVENTION

An object of the present invention is to provide an improved abdominal wound dressing for negative-pressure therapy with respect to increasing drainage capacity and user friendliness. The wound dressing shall be easy to apply, be easily adaptable to the conditions of the individual wound and be changeable without sticking together or growing together with the subsurface.

This object is, in the case of a wound dressing for use in negative-pressure therapy, achieved according to the invention by the wound dressing having a first flexible film with a first side and a second side, wherein the first side is intended for application onto exposed inner organs or for application onto the omentum majus, wherein the wound dressing is further characterized in that the wound dressing comprises at least one conduit which is applied to the second side of the first film and which consists of a pliable elastomeric material having a thickness (H) of not more than 30 mm. The conduit has at least one continuous cavity (lumen). In addition, both the conduit and the first film have openings, so that a fluid connection can be established between the conduit and the wound space. Moreover, there can be a fluid-conducting connection between the conduit and a negative-pressure source by means of at least one further, in particular terminal, opening.

Fluid in this connection is understood to mean both liquids, for example wound fluid or blood, and gases, for example air or carbon dioxide.

Compared to the wound dressings known from the prior art, the wound dressing according to the invention provides at least one further cavity in the form of a pliable conduit for draining wound exudate, as a result of which the drainage capacity is considerably increased and is, in addition, stabilized over the duration of use. The wound dressing according to the invention ensures continuous and trouble-free draining of wound fluid over the duration of use of the apparatus, for example over a period of 24 to 72 hours. It is envisaged that the wound fluid passes, alternatively or simultaneously in different ways, from the wound space to the negative-pressure source. Firstly, the wound fluid, which may be not only blood but also, for example, liquid which has escaped from the inner organs, can pass from the wound space through the openings in the first film and the conduit into the conduit. The fluid finally reaches a negative-pressure source through the at least one further opening in the conduit. Secondly, wound fluid, as in the case of the wound dressings known in the prior art, can pass from the wound space through the first film provided with openings to a negative-pressure source, if the film not only has openings in the surface areas provided with the conduit, but also has openings outside these areas. Lastly, it is also conceivable that the wound fluid is first sucked through the openings in the first film and then through openings in the conduit, if such openings are provided at a suitable site, into the lumen of the conduit. Continuous and trouble-free draining of wound fluid over the duration of use is ensured especially via the lumen of the conduit, since this, compared for example to a foam layer, is less prone to blockages owing to its cross-sectional size.

The abovementioned fluid connections of the wound dressing according to the invention ensure not only drainage of wound fluid from the wound space but also continuous and trouble-free application of negative pressure (i.e., establishing reduced air pressure with respect to ambient air pressure) in the wound space over the duration of therapeutic use.

Furthermore, the wound dressing according to the invention can, without restrictions, be adjusted to the shape and size of the wound by the user, i.e., by the physician or medical personnel, for example by simple cutting out using sterile scissors. If, in contrast, it is desired for the manufacturer to provide the product already adjusted to predefined wound shapes and wound sizes, the structure of the wound dressing according to the invention, in this regard, likewise holds no restrictions.

If, on the combination of first film and conduit applied thereto in the case of negative-pressure treatment, further layers of a dressing material are to be applied to the side facing away from the wound, the wound dressing according to the invention offers the additional advantage that contact between the additional dressing material and the floor of the wound through the openings of the film can be further reduced or completely excluded. For instance, it can be envisaged that the openings in the first film are located solely in the contact area of conduit and first film. In this case, contact between the additional dressing material and the floor of the wound through the openings of the film is completely excluded, while, however, at the same time wound fluid can drain unimpeded via the conduits to the negative-pressure source. Additional openings can also be present in the first film outside the contact area of conduit and first film. In this case as well, contact between the additional dressing material and the floor of the wound through the openings of the film is at least reduced, since the conduits act as a spacer between the additional dressing material and first film in the areas of film situated between the conduits. Such an effect can be reinforced by a suitable arrangement of the conduit on the first film, for example by an attachment of a multiplicity of closely spaced conduits.

The wound dressing according to the invention comprises a first flexible film having a first side and a second side. When used, the flexible film is laid with its first side in direct contact with the floor of the wound, i.e., more particularly the inner organs exposed as a result of surgery or injury or the omentum majus. It is therefore essential that the first flexible film consists of a material which does not stick together or grow together with the exposed inner organs or the omentum majus during the duration of use, i.e., that it has atraumatic properties.

Suitable materials for the first flexible film comprise thermoplastic films for medical purposes, more particularly films consisting of PU, PE, PET, PVC, silicone or a mixture thereof. Preferably, the thermoplastic film is a PU film.

According to a particularly preferred embodiment, the first flexible film is a PU film without a support film and having a thickness of from 50 to 60 µm, for example the product "Folie 4142 medical transparent" from Gerlinger Industries (Nördlingen, Germany).

The first flexible film has a multiplicity of openings which enable wound fluid to pass through. The openings can be holes or slits. With respect to the shape and size of the openings, adjustments can be appropriately made to achieve the desired permeability of the film to wound fluid. Round, oval, angular or, for example, star-shaped holes are conceivable. The slits can, for example, be elongated or cross-shaped slits.

If the openings are slits, they should each have a length of at least 1 mm and not more than 30 mm, preferably at least 2 mm and not more than 20 mm and more particularly at least 5 mm and not more than 10 mm. It was found that particularly a film comprising slits having a length of at least 5 mm and not more than 10 mm, between 10 and 90 of such slits being introduced on a film surface area of 100 cm$^2$, has particularly advantageous properties with respect to stability while, at the same time, having sufficient fluid permeability.

If, however, the openings are holes, the diameter thereof can be appropriately adjusted with respect to the desired fluid permeability, for example in a range from 0.1 mm to 20 mm. Ranges between at least 0.2 mm and not more than 10 mm, more particularly between at least 0.3 mm and not more than 5 mm, are particularly preferred with respect to a favorable combination of fluid permeability and atraumatic properties.

The openings can be distributed uniformly, i.e., in regularly repeating patterns, or randomly over the surface of the first film. However, it is also possible to apply the openings only in certain surface areas. More particularly, it is preferred to apply the openings only in those surface areas of the first film which are in contact with the conduit, if further dressing material is to be applied to the combination of film and conduit. Contact between the dressing material and the floor of the wound is excluded by such an arrangement.

According to a further embodiment, the openings are located only in the central area of the first film, whereas an edge area of the film is free of openings. An inverse arrangement is likewise possible.

If the openings in the first film are holes, the sum of the open area of the holes ought to be at least 0.2%, preferably at least 1%, of the areal extent of the film in order to ensure sufficient permeability of the film to wound fluid. An open area of at most 20% of the film ought not to be exceeded, since this might otherwise have an adverse effect on the stability of the first film. Preferably, the first film comprises holes which occupy less than 15% of the film.

Also conceivable is a combination of holes and slits, it being possible for certain surface areas of the first film to have holes and another surface area of the first film to have slits. For instance, there may be an advantage to providing with holes those surface areas of the first film, which is in contact with a conduit, while providing with slits a different surface area, which is arranged between the conduits. Such an arrangement of holes and slits may be desirable especially when further dressing material is applied to the combination of film and conduit, since this minimizes or completely prevents contact between the dressing material and the floor of the wound (inner organs or the omentum majus).

The invention comprises, with respect to the shape, size, number and arrangement of the openings in the first flexible film, further variants which are not specifically mentioned here.

The openings can be introduced into the first film before fastening the one or more conduits. However, it is also possible to apply the openings only after fastening the one or more conduits to the first film. The latter variant is particularly advantageous when only that surface area of the first film which is in contact with a conduit is to have openings.

According to a further embodiment, slits can be introduced into the first film before the conduit is fastened to the film. After fastening the conduit to the first film, openings can then be introduced only into that surface area of the first film which is in contact with a conduit.

The at least one conduit applied to the first film is located on the second side of the first film facing away from the wound. Typically, the edge of the combination of first film and conduit is, after application, carefully inserted between the abdominal wall and the floor of the wound. However, it may also be advantageous, with respect to the thickness of the wound dressing, to apply the at least one conduit solely in the central area of the first film, so that an edge area of the first film is present which has no conduits applied and is intended especially for insertion between the abdominal wall and the floor of the wound.

The combination of first film and conduit is intended to be altogether flexible and soft, so that the wound dressing clings tightly to the floor of the wound. The flexibility and softness of the combination of first film and conduit are determined in particular by the properties of the individual components of film and conduit. Therefore, it is essential that the conduit applied to the first film also consists of a pliable elastomeric material. According to a preferred embodiment, the conduit should therefore be made of a material which has a Shore A hardness of not more than 60 (determined in accordance with DIN 53505 of August 2000, specifically at 23° C. on a 6 mm thick level and smooth plate-like test specimen as described in the standard). It is particularly advantageous to use even softer materials for the conduit, i.e., materials having a Shore A hardness of less than 50, more particularly having a Shore A hardness of less than 45, particularly preferably having a Shore A hardness of less than 40. In addition, a combination of first film and conduit can be cut to shape with particular ease when the Shore A is not more than 60, preferably less than 50, particularly preferably less than 45, more particularly less than 40. This facilitates adjusting the wound dressing to the wound shape.

The conduit is preferably a drainage tube, more particularly a drainage tube for medical purposes, comprising, for example, PU (polyurethane), PVC (polyvinyl chloride), PE (polyethylene), PET (polyethylene terephthalate), PTFE (polytetrafluoroethylene), silicone or a mixture thereof.

Furthermore, with respect to the flexibility of the combination of first film and conduit, it is essential that the conduit has a thickness (H) of not more than 30 mm, preferably less than 20 mm, more particularly less than 15 mm.

The conduit ought to have in each case a multiplicity of openings which enable wound fluid to pass through from the wound space, more particularly from the abdominal cavity, into the lumen of the conduit. Here, it is advantageous that at least a sufficient proportion of the openings of the conduit lie over the openings in the first film, so that liquid can pass over from the wound space directly into the lumen of the conduit. The openings in the conduit are holes, and there are no restrictions in principle with respect to shape, arrangement and size. Preferably, the holes are round, oval or angular, and ought to have an open area in each case of at least 0.5 mm$^2$.

Furthermore, the conduit has at least one further, terminal opening which enables fluid communication with a negative-pressure source.

The conduit applied to the first film preferably has an altogether planar form with respect to its exterior dimensions. An altogether planar form of the conduit, in the context of the invention, is understood to mean that the ratio of the transverse extent or width of the conduit (diameter of the conduit in a plane parallel to the first film) to the thickness or height of the conduit (H; diameter of the conduit in a plane perpendicular to the first film) is more than 1.25, preferably more than 1.5, with the thickness (H) being not more than 30 mm, preferably less than 20 mm, more particularly less than 12 mm. According to a particularly preferred embodiment of the invention, the width is between 8 mm and 40 mm, more particularly between 15 and 35 mm.

According to a further particularly advantageous embodiment, the conduit can be indissolubly and extensively bound to the second side of the first film with at least 70%, preferably 80%, of its area projected perpendicularly onto the first film. Particularly preferably, the conduit is a drainage tube having altogether substantially rectangular exterior dimensions, in which at least 90% of its area projected perpendicularly onto the first film can be indissolubly and extensively bound to the second side of the first film.

The altogether planar form is, firstly, advantageous for ensuring a stable and, where appropriate, indissoluble bond with the first film during use. Secondly, the planar form provides a sufficiently large contact area, so that a multiplicity of openings reaching through the first film and second film can be provided.

The conduit has a lumen in the form of one or more continuous hollow spaces in order to ensure drainage of wound fluid to the negative-pressure source, and to ensure negative pressure in the wound space. Accordingly, the conduit can comprise either only one hollow space or two or more hollow spaces in order to form the lumen.

If the conduit has two or more hollow spaces, the individual hollow spaces can be connected to one another via openings in order to form a continuous lumen. However, it is also conceivable for the conduit to have two or more hollow spaces which proceed continuously and which are not connected to one another. The total open transverse-sectional area of the lumen should be at least 1 mm², preferably at least 5 mm², in order to provide sufficient flow capacity for the drainage of wound fluid. More particularly, the lumen of the conduit ought to have a transverse-sectional area of altogether from 10 to 50 mm², preferably from 20 to 35 mm². "Total open transverse-sectional area of the lumen" in this content is understood to mean the sum of the open transverse-sectional areas of the individual hollow spaces of an individual conduit, with the conduit being in an uncompressed state.

Preferably, the conduit comprises only two or three continuous hollow spaces which, in particular, have a fluid-conducting connection to one another.

According to a further particularly preferred embodiment, the conduit has only a single continuous hollow space.

Furthermore, the conduit has to have sufficient stability to negative pressure. The expression "negative pressure in the wound space" in the context of the invention refers to reduced air pressure within the bandage with respect to ambient air pressure (atmospheric air pressure). "Within the bandage" is understood to mean the space formed by the covering material and the wound.

The pressure difference between air pressure within the bandage and ambient air pressure in the context of the invention is specified in mmHg (millimeter of mercury), since this is customary in the field of negative-pressure therapy. 1 mmHg corresponds to one Torr or 133.322 Pa (Pascal). In the context of the invention, negative pressure, i.e., the pressure difference between air pressure within the bandage and ambient air pressure, is specified in mmHg as a positive numerical value. Sufficient stability to negative pressure is understood to mean that the conduit maintains an open transverse section of at least 1 mm² under a typical negative pressure of 125 mmHg used in negative-pressure therapy. Undesired compression of the conduit under negative pressure can be prevented in different ways known to a person skilled in the art, for example by means of appropriate transverse-sectional geometry and/or by selecting suitable materials. For example, asymmetrically arranged inner wall ribs which have an advantageous effect on the stability of the conduit to negative pressure can be provided in the conduit. Suitable conduits according to the invention having sufficient stability to negative pressure are also commercially available as a finished product of a quality suitable for medical applications. Such conduits are usually referred to as drainage tubes. For example, Primed (Halberstadt, Germany) offers planar drainage tubes of different dimensions under the name "J. P. Flachdrain".

According to a particularly advantageous embodiment, the conduit is coated with an anticoagulatory substance (for example, heparin, or another anticoagulatory substance usually used for coating medical tubes or tubing). Such an anticoagulatory coating can prevent blockage of the conduit owing to blood clots, and so a consistently high flow rate of wound exudate is ensured over a prolonged duration of use. Medical drainage tubes coated with an anticoagulant are commercially available as a finished product, for example from Axiom Medical (Bürstadt, Germany).

According to the invention, it is envisaged that at least one conduit is applied to the second side of the first film. At least one conduit in this context is understood to mean that either one or two or more separate units of the conduit are applied to the first film.

If only one conduit is provided, the conduit is preferably applied to the second side of the first film in a spiral arrangement, with one end of the conduit lying in the center or near the center of the first film.

Preferably, the wound dressing according to the invention comprises more than one conduit, i.e., two or more separate units of the conduit, which, in particular, are applied to the first film in a radial arrangement.

Alternatively, two or more conduits can be applied to the first film in a substantially parallel arrangement. Between the parallel strands, further units of the conduits can be provided as cross-connections. Accordingly, the invention comprises a wound dressing in which at least three conduits are applied to the second side of the first film in a substantially parallel arrangement and in which, in addition, cross-connections are provided between the conduits, so that the cross-connections can establish fluid communication between the conduits.

The conduit is applied to the second side of the first film. In the context of the present invention, this is understood to mean that either a) the conduit is indissolubly and extensively bound to the second side of the first film and/or b) the conduit on the second side of the first film is held on the film by fasteners.

In the case of the first option a), the conduit in particular ought to be indissolubly and extensively bound to the second side of the first film with at least 70% of its area projected perpendicularly onto the first film, since, in this way, sufficient stability and strength of the combination of first film and conduit is ensured.

In the case of the second option b), the conduit in particular ought to lie on the second side of the first film with at least 85% of its area projected perpendicularly onto the first film, with the conduit being held on the first film by fasteners. A fastener is understood to mean a multiplicity of fasteners known to a person skilled in the art, for example adhesive strips or clips. More particularly, it is also possible to apply a further layer, more particularly a further flexible film, in such a way that the conduit is held stably between the first film and further film. A further film applied in this way, which holds the one or more conduits on the first film in the form of a pocket for example, is covered by the term fastener. In the context of this embodiment, it is preferred that there is no adhesive bonding between the conduit and one of the two films. Instead, there is an indissoluble bond between the first film and further film.

According to a particularly advantageous embodiment of the invention, the wound dressing comprises a flexible conduit plate which is suitable for receiving a terminal region of the at least one conduit. The conduit plate is preferably attached or laid in the central area of the side of the combination of first film and conduit or—if present—of the combination of first film, conduit and second film facing away from the wound during use. The conduit plate comprises appropriately a medically suitable plastic, for example consisting of PU (polyurethane), PVC (polyvinyl chloride), PE (polyethylene), PET (polyethylene terephthalate), PTFE (polytetrafluoroethylene), silicone or a mixture thereof. With respect to use, it is advantageous for the conduit plate to be altogether soft and flexible. Preferably, the conduit plate should consist of an elastomeric material which has a Shore A hardness of not more than 80, preferably not more than 70 and more particularly not more than 60. The conduit plate can be indissolubly fastened on the second side of the first film. It is envisaged in particular that the conduit plate is fastened on the combination of film(s) and conduits in such a way that it is located under a negative-pressure connecting piece during the duration of negative-pressure therapy. The conduit plate should be matched to the negative-pressure connecting piece as far as possible with respect to its areal extent. This is understood to mean that the conduit plate has an area projected onto a base which largely corresponds to the negative-pressure connecting piece area projected onto a base. The conduit plate and negative-pressure connecting piece areas projected onto a base should ideally deviate by less than 50% from one another. Such an arrangement contributes to stabilizing the wound dressing and can contribute to reducing undesired mechanical effects on the floor of the wound.

According to a simple embodiment, the conduit plate is used as a supporting plate merely for correctly positioning the one or more conduits. In this embodiment, the conduits, which have an opening in the region of the conduit plate, are fastened to the conduit plate.

According to a further embodiment, the conduit plate forms a central hollow space, in terms of a planar socket, with the central hollow space having a fluid-conducting connection to the lumina of the one or more conduits via an opening, more particularly via an open end of the conduit. The hollow space of the conduit plate has passages on the side facing away from the wound, so that fluid communication with the negative-pressure connecting piece can be established.

The conduit plate can be round, square or polygonal and has a diameter of at least 1 cm and not more than 12 cm, more particularly at least 2 cm and not more than 10 cm.

According to a very advantageous embodiment of the invention, the wound dressing additionally comprises a second flexible film, with the second film being applied to the side of the combination of first film and conduit facing away from the wound during use. Preferably, the second film is made of a highly fluid-impermeable material. To produce the second flexible film, use can be made of, in particular, the materials and finished products already mentioned above in connection with the first flexible film, for example thermoplastic films for medical purposes, more particularly films consisting of PU, PE, PET, PVC, silicone or a mixture thereof.

According to one embodiment, the second film can have a multiplicity of openings distributed over the surface.

Preferably, the second film is, however, highly fluid impermeable and has only a single opening preferably arranged in the central area.

The second film is indissolubly fastened on the combination of first film and conduit, for example by adhesion or by thermal welding. Suitable fastening sites include either the conduit and/or those areas of the first flexible film which are located between the conduits.

The second flexible film optionally comprised by the wound dressing according to the invention can advantageously contribute to improving the stability and manageability of the wound dressing. Furthermore, it is possible, through a suitable combination of first flexible film and second flexible film, to appropriately modify and optimize the permeability of the wound dressing to wound fluid, and the atraumatic properties of the wound dressing. This can contribute to improved and accelerated wound healing, since wound fluid can be removed efficiently from the wound space and damage to the floor of the wound, or to the exposed inner organs or the omentum majus, is reduced.

According to one embodiment of the wound dressing, the second film has a multiplicity of openings distributed over the surface which are suitable for conducting fluid. It may prove to be advantageous for the openings present in the first film and the openings present in the second film to be arranged such that the openings do not substantially overlap with one another. "Not substantially overlapping with one another" in this context is understood to mean that openings of the first and second films overlapping with one another are present by chance at most and only in a small number. More particularly, at least 90% or 95% of the openings in the first film ought not to overlap with an opening in the second film.

According to a further preferred embodiment, the second film is highly fluid impermeable and has only a single opening preferably arranged in the central area.

According to the invention, the second film can be arranged in different ways on the combination of first film and conduit. Exemplary embodiments are presented below, although further arrangements are conceivable and are comprised by the invention.

According to a first embodiment, the second film is adhesively bonded to the at least one conduit, producing a stable combination of first film, conduit and second film. This is technically simple to achieve, for example by coating the side of the conduit pointing away from the first film with an adhesive on its surface and laying the second flexible film onto the conduit prepared in this way.

According to a further embodiment, the second film is directly adhesively bonded to the first film, but not to the conduit. The first film and second film can be adhesively bonded in a planar, punctiform or linear manner. It is also conceivable for the first film and second film not to be adhesively bonded, but brought into an indissoluble bond with one another by welding. Welding can be carried out in particular in a punctiform manner or along welding seams. A direct, indissoluble bond of first and second films results in a particularly stable arrangement.

According to a further embodiment, it is also possible to adhesively bond the second film to the first film and to the conduit. This results in a particularly stable combination.

According to a particularly advantageous embodiment, the second film is fastened on the first film by punctiform adhesion or welding in the areas outside the conduits. In particular, a multiplicity of adhesion points distributed over the surface can be provided. Such a bond of first and second films produces a fluid-conducting space between the films which can advantageously promote the drainage of wound exudate. It is preferred that the first film has a multiplicity of openings distributed over the entire surface and, furthermore, the one or more conduits have lateral openings. Wound exudate from the space which is formed by the first and second films can be sucked off via the lateral openings of the conduits. In the particularly advantageous embodiment, mentioned here, of the invention, conduits and—if present—conduit plate are located between the two films in a pocket, and are held in this way on the first film. Welding of the first and second films serves here as a fastener for the conduit, and so adhesion of the conduit to the first film can be omitted. Here, the at least one conduit should lie on the second side of the first film with at least 85% of its area projected perpendicularly onto the first film.

When using the wound dressing to temporarily cover large-area wounds of the abdominal region, the edge area of the first film or the edge area of the combination of first film, conduit and—if present—second film is usually introduced between the abdominal wall and the floor of the wound or onto the omentum majus. For this purpose, use is typically made of a planar surgical instrument, for example an abdominal or intestinal spatula. Applying the edge area of the wound dressing between the abdominal wall and the floor of the wound places great technical demands on the surgeon and is associated with a risk of injury to the inner organs. It has been found in particular to be difficult to apply the edge area of the wound dressing under the abdominal wall without any creases. It has now been found that the wound dressing can be introduced substantially more safely, more quickly and, at the same time, largely without creases into the region between the abdominal wall and the floor of the wound when the wound dressing has, on the side of the combination of first film and conduit or of the combination of first film, conduit and second film facing away from the wound during use, at least one or more pockets which are on the periphery and open toward the middle of the wound dressing and have a depth of not more than 6 cm. The treating physician can insert the abdominal or intestinal spatula into the pockets and then introduce the edge area of the wound dressing between the abdominal wall and the floor of the wound.

Such pockets, which facilitate uniform application and laying out of the combination onto the exposed inner organs or onto the omentum majus, can be formed in particular by folding the first and/or second films or by applying additional film pieces.

Accordingly, the present invention comprises, according to a preferred embodiment, a wound dressing which has, on the side of the combination of first film and conduit or of the combination of first film, conduit and second film facing away from the wound during use, at least one or more pockets which are on the periphery and open toward the middle of the wound dressing and have a depth of not more than 6 cm, and which facilitate uniform application and laying out of the combination onto the exposed inner organs or onto the omentum majus, wherein the pockets are preferably formed by folding the first and/or second films and/or by applying film pieces. More particularly, the one or more pockets are provided on at least 50% of the extent of the combination of first film and conduit or of the combination of first film, conduit and second film.

Furthermore, it has been found to be very advantageous for the wound dressing to comprise at least one further liquid-permeable layer on the side pointing away from the wound. According to a further embodiment of the invention, the wound dressing therefore comprises at least one further liquid-permeable layer for application onto the side of the combination of first film and conduit or of the combination of first film, conduit and conduit plate or of the combination of first film, conduit and second film or of the combination of first film, conduit, conduit plate and second film facing away from the wound during use. The liquid-permeable layer preferably comprises a porous foam material, more particularly a porous polymer foam material. Particularly suitable are open-cell polymer foam materials. In the context of this application, the term open cell means that the foam material (c) contains at least 60% open cells, preferably at least 90% open cells, more preferably at least 98% open cells, more particularly essentially 100% open cells, based on the total number of cells.

Suitable materials for a porous foam material comprise, for example, polyurethane, polyurethane/polyurea copolymers, polyvinyl alcohol (PVA) or silicone.

Alternatively or additionally, the liquid-permeable layer can comprise textile materials, such as wovens or nonwovens, suitable for medical purposes, for example a nonwoven fabric consisting of synthetic polymers such as polyamide, polyester or polypropylene.

In the context of the present invention, the porous foam materials described in the German patent application DE102010034819 can be used particularly advantageously to produce the one or more liquid-permeable layers. Reference is hereby made to the content of the German patent application DE10201003481. The foam materials described in DE 102010034819.8 release foam particles only to a minimal extent or not at all when any cutting out is required for adjustment to the wound shape. Released foam particles which reach the wound may irritate the wound and impair wound healing.

Particularly advantageously, the open-cell polyurethane foam material VivanoMed sold by the applicant Paul Hartmann A G (Heidenheim, Germany) can be used as a liquid-permeable layer.

The at least one further liquid-permeable layer can improve the softness and tolerability of the wound covering and make an additional contribution to draining wound exudate.

Furthermore, in order to promote primary wound closure, it is in particular very advantageous to attach a porous polymer foam material such that the foam material is in direct contact with the wound edges.

The at least one further liquid-permeable layer has a thickness of from 2 mm to 50 mm, preferably from 3 mm to 30 mm.

The further liquid-permeable layer, which preferably comprises a porous polymer foam material, can cover the entire surface of the combination of conduit and first film (or, if present, of the combination of first film, conduit and second film). However, it is also possible for the liquid-permeable layer to be present only on part of the surface of the first or—if present—second film. Particularly when using the wound dressing as a temporary wound closure, it has been found to be favorable for a porous polymer foam material to be applied to the first or—if present—second film such that the edges of the foam material are in direct contact with the wound edges, while the first film or the combination of film(s) and conduit(s) is inserted between abdominal wall and inner organs. In such an embodiment, the liquid-permeable layer consequently lies only on a central part of the combination of first film and conduit or of the combination of first film, conduit and second film.

If the conduits are connected by means of a centrally arranged conduit plate, it may be advantageous for the further liquid-permeable layer to have a corresponding recess for accommodating the conduit plate. The recess can be merely an indentation or, alternatively, a continuous opening.

In the context of the present invention, it is also possible to provide more than one liquid-permeable layer on the side of the combination of first film and conduit or of the combination of first film, conduit and second film facing away from the wound during use, more particularly more than one layer of a porous polymer foam material. The multiple layers can be of different dimensions and of different thicknesses.

Furthermore, the wound dressing according to the invention can comprise an air-impermeable covering material for air-tight closure of the wound and of the wound surroundings, with the covering material preferably having an adhesive edge for fastening the covering material on the intact skin surrounding the wound. "Air-tight closure" is not to be understood here to mean that no gas exchange at all takes place between the wound space and its surroundings. Rather, "air-tight closure" in this context means that the negative pressure required for the negative-pressure wound therapy can be maintained, taking into account the negative-pressure pump used. Therefore, use can also be made of covering materials which have slight gas permeability, provided the negative pressure required for the negative-pressure therapy can be maintained.

In a preferred embodiment of the invention, the covering material comprises a water-insoluble polymer or a metal film for air-tight closure of the wound.

In a particularly preferred embodiment of the invention, the water-insoluble polymer is polyurethane, polyester, polypropylene, polyethylene, polyamide or polyvinyl chloride, polyorganosiloxane (silicone), or is a mixture thereof.

Finished products which have the abovementioned properties can also be used as covering material.

Hydrofilm® (Paul Hartmann A G, Germany) and Visulin® (Paul Hartmann A G, Germany) polyurethane films have been found to be particularly suitable covering materials for the apparatus according to the invention.

The covering material is fastened in the wound surroundings or on the wound edge such that an air-tight wound closure is ensured. It may be useful for the covering material to be self-adhesive over the entire surface or to have a self-adhesive edge. Alternatively, fastening and sealing can, for example, be carried out with an adhesive film, with a liquid adhesive or with a sealing compound.

In a preferred embodiment of the invention, the covering material comprises a film consisting of one or more water-insoluble polymers, with the film being self-adhesive over the entire surface or having a self-adhesive edge.

In the context of the wound dressing according to the invention, a negative-pressure connecting piece for functional connection of the wound space to a negative-pressure source located outside the wound dressing is also claimed, wherein the negative-pressure connecting piece is designed such that negative pressure can be established in the wound space and liquids can be sucked off from the wound space. When using the wound dressing in negative-pressure wound therapy, the negative-pressure connecting piece is preferably attached to the side of the air-impermeable covering material facing away from the wound, the covering material having suitable openings. Negative-pressure connecting pieces are also known to a person skilled in the art by the term "port". The negative-pressure connecting piece usually comprises a connecting line, and a negative-pressure adaptor, so that it can be connected to the further components of the negative-pressure system.

According to a further preferred embodiment, the covering material and the means for functional connection of the wound space to a negative-pressure source located outside the covering material are already provided connected to one another, ready for use. It is very particularly preferred for this embodiment to comprise a film which consists of one or more water-insoluble polymers and which has a self-adhesive edge, since this arrangement substantially facilitates application of the dressing.

For the wound dressing described in the present invention, the negative-pressure connecting pieces disclosed in German patent applications DE 10 2010 003 273.1, DE 10 2010 003 272.3 and DE 10 2009 060 596.7 are particularly suitable.

According to an alternative embodiment, the functional connection of the wound space to a negative-pressure source located outside the covering material can be established with at least one connecting line. The at least one connecting line can be fed through the covering material. Alternatively, the at least one connecting line can be conducted under the edge of the covering material. In both cases, the entry site must be sealed air tight, so that the desired negative pressure in the dressing can be maintained. Suitable sealants are, for example, an adhesive film, an adhesive composition or an adhesive strip.

The connecting line can, for example, be a tube, tubing or another body having a hollow space. A suitable tube is, for example, a silicone drainage tube.

Furthermore, the wound dressing according to the invention can comprise a device, for checking and, if necessary, adjusting the negative pressure actually present in the apparatus. The device can be located in the wound space or at another suitable site.

Alternatively, it is also possible to attach a pressure sensor in the negative-pressure line between the bandage and the negative-pressure source.

It is envisaged that the abovementioned components are provided as a ready-to-use set (kit) for the physicians and trained personnel carrying out the wound treatment. The invention therefore also relates to a ready-to-use set for negative-pressure wound treatment, comprising a) a wound dressing according to any of claims 1 to 14, b) at least one liquid-permeable layer for application onto the side of the wound dressing facing away from the wound during use, wherein the at least one liquid-permeable layer preferably comprises one or more flat pads consisting of a porous polymer foam material, more particularly PU, PVA or silicone, c) an air-impermeable covering material for air-tight closure of the wound and of the wound surroundings, wherein the covering material preferably has an adhesive edge, d) a negative-pressure connecting piece for functional connection of the wound space to a negative-pressure source located outside the covering material, so that negative pressure can be established in the wound space and liquids can be sucked off from the wound space, wherein the negative-pressure connecting piece is preferably intended for attachment to the external side of the covering material facing away from the wound during use and wherein all of components a) to d) are each individually sterile packed.

In a particularly preferred embodiment of the set, component a) is, in particular, a combination of first film, conduit, conduit plate and second film, since such a combination, as already explained in more detail, has particularly favorable properties with respect to fluid permeability during use and can, during change of dressing, be detached without sticking together with the exposed inner organs or with the omentum majus. Furthermore, it is desirable for pockets according to claim 19 to be provided in the wound dressing.

Negative-pressure connecting pieces particularly suitable for the ready-to-use set are described in the German patent applications having application numbers DE 10 2010 003 273.1, DE 10 2010 003 272.3 and DE 10 2009 060 596.7.

Furthermore, the set can comprise optional constituents such as, for example, one or more additional flat elements of a liquid-permeable layer, adhesives for fixing the dressing, sealants for establishing an air-impermeable seal of the dressing, pressure sensors, connecting elements for pressure sensors, tubes, connecting pieces for tubes, disinfectants, skin care products, pharmaceutical preparations or instructions for use.

Furthermore, the set preferably comprises a ready-to-use negative-pressure unit. The negative-pressure unit can comprise components such as, for example, a pump, one or more liquid containers, a control unit, a power supply, electrical connectors and tubes. The negative-pressure unit can also comprise an apparatus for functional connection of the negative-pressure dressing to an available stationary negative-pressure source.

Negative-pressure units particularly suitable for the ready-to-use set are described in the German patent applications having application numbers DE102009038130.9 and DE102009038131.7. A negative-pressure unit particularly suitable for the set is commercially available under the name VivanoTec (manufacturer: Paul Hartmann A G, Heidenheim, Germany).

Preferably, all components for which it is medically necessary are provided sterile packed. The advantage of the ready-to-use sets is that the negative-pressure dressing can be applied in a rapid, standardized and uncomplicated manner. A further advantage is that all constituents of the set used in the wound region can be provided presterilized.

FIGURE LEGENDS

1. First flexible film
2. Conduit
3. Hollow space (lumen) in conduit
4. Second flexible film
5. Opening in first flexible film, which overlaps with an opening in the conduit
6. Opening in first flexible film, which does not overlap with an opening in the conduit
7. Adhesion or fastening point between first and second film
8. Conduit plate
9. Opening in conduit plate
10. Central opening in second film
11. Liquid-permeable layer
12. Space between floor of the wound (for example, omentum majus or exposed inner organs) and abdominal wall
13. Floor of the wound (for example, omentum majus or exposed inner organs)
14. Abdominal wall
15. Wound edge
16. Air-impermeable covering film
17. Opening in covering film
18. Negative-pressure connector (port)
19. Negative-pressure line
20. Canister for wound exudate
21. Negative-pressure source
22. Opening in the wall of the conduit
23. Terminal opening in conduit
24. Hollow space in conduit plate
25. Pocket open toward the middle of the wound dressing
26. Seam or adhesion region of pocket with first or second flexible film
27. Opening of the pocket pointing toward the middle of the wound dressing
28. Lumen of the negative-pressure line

BRIEF DESCRIPTION OF THE DRAWINGS

The apparatus according to the invention for negative-pressure wound therapy is explained in more detail below by means of schematic drawings. However, the invention is not to be understood to be reduced to the embodiments presented in the drawings or in the description of the drawing. On the contrary, the apparatus according to the invention also comprises combinations of the individual features of the alternative forms.

DETAILED DESCRIPTION OF THE INVENTION

Figure 1:
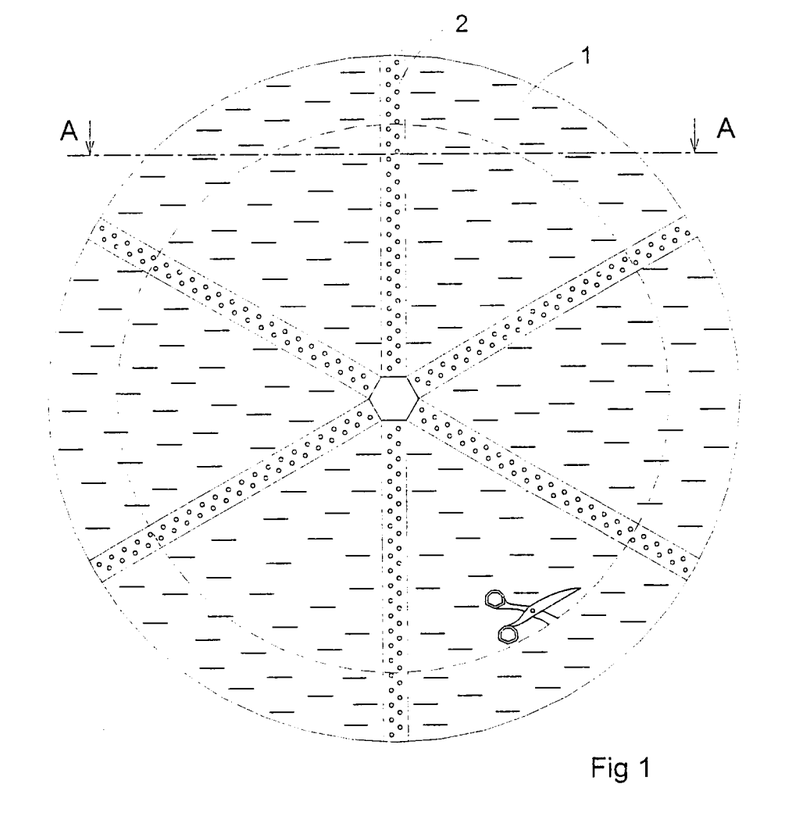
FIG. 1 shows one embodiment of the wound dressing according to the invention for use in negative-pressure therapy as a top view of the side of the wound dressing facing away from the wound.
Figure 2:
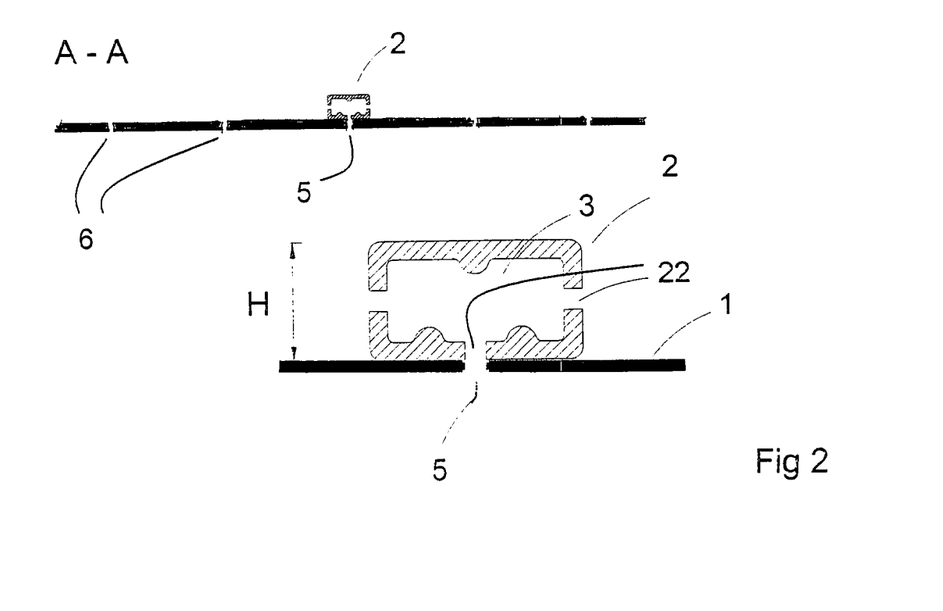
FIG. 2 shows a transverse section of the wound dressing presented in FIG. 1 along the line A-A.

In the embodiment shown in FIG. 1 and FIG. 2, multiple segments of a conduit (2) consisting of a pliable elastomeric material having a thickness (H) of not more than 30 mm are arranged radially on a first flexible film (1). The conduit (2) has a multiplicity of lateral openings (22) and at least one terminal opening (23). It is advantageous for the conduit (2) to be indissolubly bound to the first film (1), for example by adhesion. The conduit (2) ought to be planar, so that it can be indissolubly and extensively bound with at least 70% of its area projected perpendicularly onto the first film (1). Planar in this context is understood to mean that the ratio of width to height (H) of the conduit ought to be at least 1.25, more particularly at least 1.50. The conduit (2) should ideally be made of an elastomeric material which has a Shore A hardness of not more than 60, preferably less than 50, particularly preferably less than 45, more particularly less than 40. As shown by the scissors symbol in FIG. 1, the wound dressing can be adjusted by cutting out to the size required for treating the wound, with both the first film (1) and the conduit (2) being cut through. As per FIG. 2, the first film (1) can have both openings (6) in the areas not in contact with the conduit (2), and openings (5) which overlap with the openings (22) in the conduit (2). As shown in FIG. 2 (enlarged section), openings (5) of the first film (1) and conduit (2) overlapping with one another enable direct fluid communication between the wound space and lumen (3) of the conduit (2). In order to obtain such overlapping openings (5) through the first film (1) and conduit (2), it is simplest to introduce the openings only after adhesively bonding the conduit and first film. As per the particularly advantageous embodiment of the invention shown in FIG. 2 (enlarged section), the conduit (2) has both laterally applied openings (22), and openings in the wall facing the first film (1). However, the invention is not restricted to the arrangement of openings (22) in the conduit (2) shown in FIG. 2. On the contrary, the openings (22) can be present only at one, two, three or else at all exterior walls of the conduit (2). As per the embodiment shown in FIG. 2, the conduit has in addition highly rectangular exterior dimensions with respect to its transverse section. Other exterior shapes are also conceivable, provided the conduit (2) is altogether planar. On the inner side pointing toward the lumen (3), the conduit can have protrusions or bulges, which serve to stabilize the conduit (2).

Figure 3:
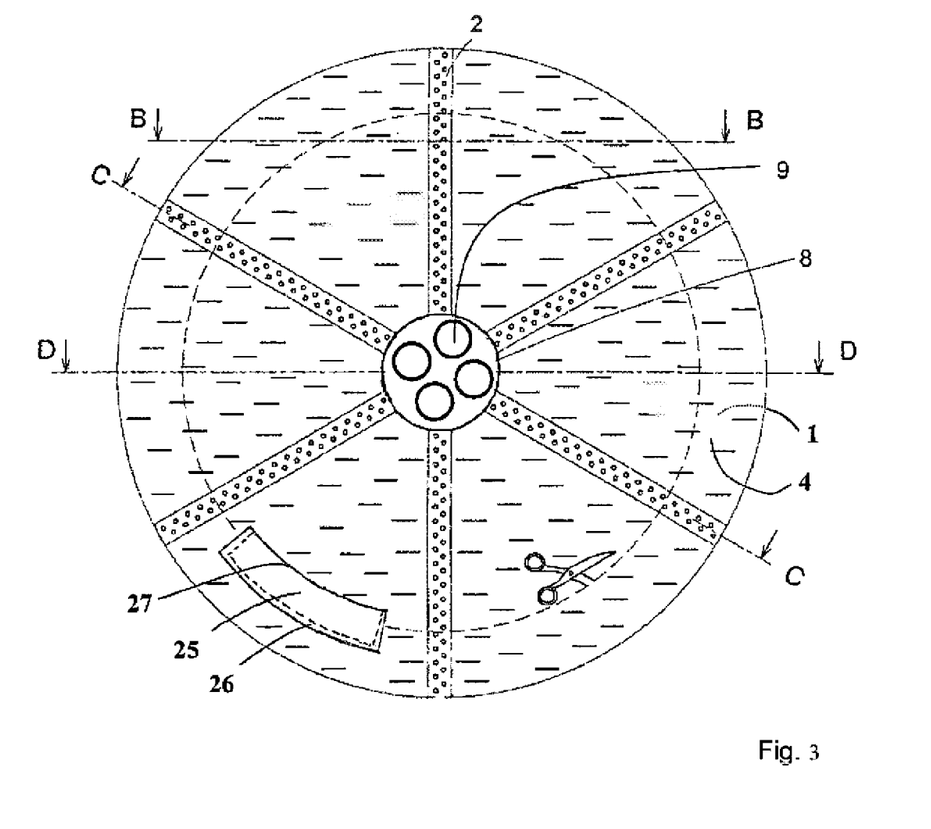
FIG. 3 shows a further embodiment of the wound dressing according to the invention as a top view of the side of the wound dressing facing away from the wound.
Figure 4:
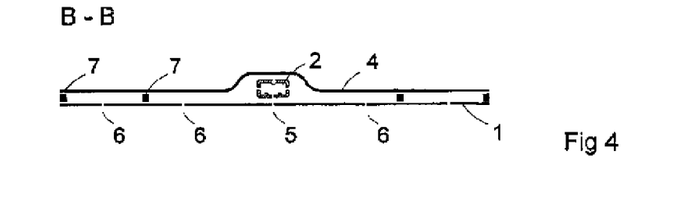
FIG. 4 shows the embodiment as per FIG. 3 as a transverse section along the line B-B.
Figure 5:
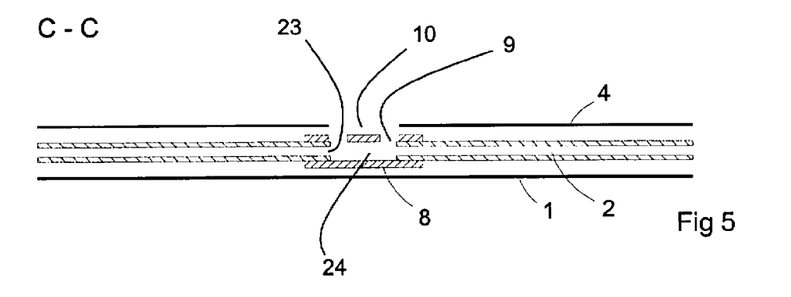
FIG. 5 shows the embodiment as per FIG. 3 as a transverse section along the line C-C.
Figure 6:
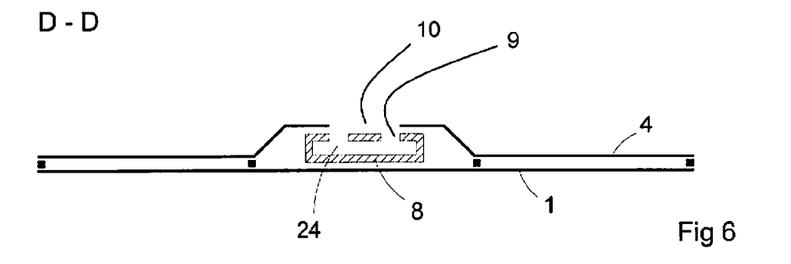
FIG. 6 shows the embodiment as per FIG. 3 as a transverse section along the line D-D.

A further preferred embodiment is shown in FIG. 3 (top view), and in FIG. 4, FIG. 5 and FIG. 6 (transverse sections). According to this embodiment, the wound dressing comprises a second flexible film (4) which is applied to the combination of first flexible film (1), conduit (2) and conduit plate (8). In the embodiment shown, the second flexible film (4) is a transparent film (in the top view of FIG. 3, the further components arranged below the second film are therefore shown as if the second film were not present). The conduits (2) are arranged radially and have a liquid-conducting connection in the center by means of a conduit plate (8). The conduit plate (8) is in the form of a planar socket having a hollow space (24) and can be indissolubly bound to the first flexible film (1) and/or the second flexible film (4), for example by adhesion. According to a particularly advantageous development of the invention, the second flexible film (4) is highly fluid impermeable and has only a single opening (10) preferably arranged in the central area. An indissoluble bond of the second flexible film (4) to the conduit plate (8) is particularly advantageous in this embodiment.

Wound fluid can initially find its way from the wound into the lumen (3) of the conduit (2) via openings (5, 22) in the first film (1) and in the conduit (2). Additionally, wound fluid can initially find its way into the space between the first (1) and second films (4) via openings (6) in the first flexible film (1) and then find its way into the lumen (3) of the conduit (2) via openings (22) applied laterally on the conduit. From the lumen (3) of the conduit (2), wound fluid can in addition be sucked into the lumen (24) of the conduit plate (8). The lumen (24) of the conduit plate (8) is in fluid communication with a negative-pressure connection via openings (9) in the conduit plate (8) which are located removed from the wound. It is particularly advantageous for the first (1) and second films (4) to be indissolubly bound to one another via adhesion points (7). In such an embodiment, it is additionally possible to omit adhesion of one or more conduits (2) to the first (1) and/or second films (4), since they are held by the two films acting as a pocket. However, particularly in this embodiment, it is useful to adhesively bond the second flexible film (4) to the edge area of the conduit plate (8). The punctiform bond of the first (1) and second (4) films produces a space which enables fluid flow. Here, it is desirable for the conduits (2) to have lateral openings (22), so that fluid can drain from the space into the lumen (3) of the conduits (2).

The conduits (2) have a fluid-conducting connection to the conduit plate (8) (FIG. 5). This is achieved by a conduit (2) open at one end being inserted into an opening of the conduit plate (8) or being fastened in another way, and so the conduit has a fluid-conducting connection (2) to a negative-pressure source (21) by means of at least one terminal opening (23). The conduit plate (8) can be indissolubly bound to the first flexible film (1), for example by adhesion, or alternatively lie loosely on the first flexible film (1). The conduit plate (8) has one or more openings (9) at the top, i.e., at the side pointing away from the wound during use. As can be seen in FIG. 5, the conduit plate (8) is located between the first film (1) and the second film (4). The second flexible film (4) has a central cutout (10), and so fluid communication between the hollow space (24) of the conduit plate (8) and a negative-pressure connector (port) can take place. Expediently, as shown in FIG. 5 and FIG. 6, the central opening in the second flexible film (4) is formed such that the inner edges of the film (4) lie on the upper (i.e., pointing away from the wound during use) peripheral areas of the conduit plate (8) and are indissolubly bound to one another there. This can, for example, be achieved by adhesion. Binding the second flexible film (4) to the conduit plate (8) can, as is shown in FIG. 5 and FIG. 6, be achieved in particular by adhesively bonding the second flexible film (4) to the peripheral area of the upper (i.e., pointing away from the wound during use) side of the conduit plate (8).

FIG. 3 shows in addition a pocket (25) open toward the middle of the wound dressing and having a depth of not more than 6 cm. FIG. 3 shows only one pocket by way of example. Preferably, however, two or more pockets of this kind, distributed around the circumference of the wound dressing and spaced apart as evenly as possible, should be applied. More particularly, the one or more pockets are provided on at least 50% of the circumference of the wound dressing.

Such pockets (25) facilitate uniform application and laying out of the wound dressing onto the floor of the wound (13). More particularly, the pockets facilitate the insertion of the wound dressing between the floor of the wound (13) and the abdominal wall (14), for example by means of an abdominal spatula. The pockets (25) can be formed by folding the edge of the first flexible film (1) or of the combination of first (1) and second film (4) and/or by applying further film pieces. In the exemplary embodiment shown in FIG. 3, the pocket (25) is formed by applying a further film piece. The film piece is fastened to the second flexible film (4) by a seam or adhesive (26) and has an opening (27) pointing toward the middle of the wound dressing. It is also possible to attach two or more concentrically applied rows of pockets. This has the advantage that, when cutting out the edge of the wound dressing (insofar as pockets are partly or completely cut off), additional intact pockets attached further within are available, which facilitate introduction of the wound dressing between the floor of the wound (13) and the abdominal wall.

Furthermore, one or more liquid-permeable layers can be applied to the side of the second film pointing away from the wound during use. A particularly suitable material for such a liquid-permeable layer comprises a porous polymer foam, more particularly an open-cell porous polymer foam. When using a fluid-permeable layer which is arranged over the second flexible film (4), fluid communication can be achieved from the hollow space (24) of the conduit plate (8) to a negative-pressure connector (port) via the liquid-permeable layer.

FIG. 6 shows a section along the line D-D of FIG. 3. Located in the center of the wound dressing is the conduit plate (8) having openings (9) pointing toward the top. The edges of the second flexible film (4) rest on the edge of the conduit plate (8) and are preferably indissolubly bound to the edge, for example by adhesion. In the peripheral areas outside the conduit plate (8), the first flexible film (1) and the second flexible film (4) are in direct contact with one another. Preferably, the first (1) and second (4) films are bound via adhesion points (7). The adhesion points (7) can result in a slight spacing between the first (1) and second (4) films. In the embodiment shown in FIG. 6, the first flexible film (1) has a multiplicity of openings (5, 6) distributed over the surface of the first film, whereas the second film (4) only has a single central opening (10). In this arrangement, a liquid-permeable layer can be optionally applied to the side of the second film (4) pointing away from the wound, without the fluid-permeable layer coming into contact with the floor of the wound.

This is advantageous, since, in this way, adhesion of the fluid-permeable layer to the floor of the wound is avoided.

Figure 7:
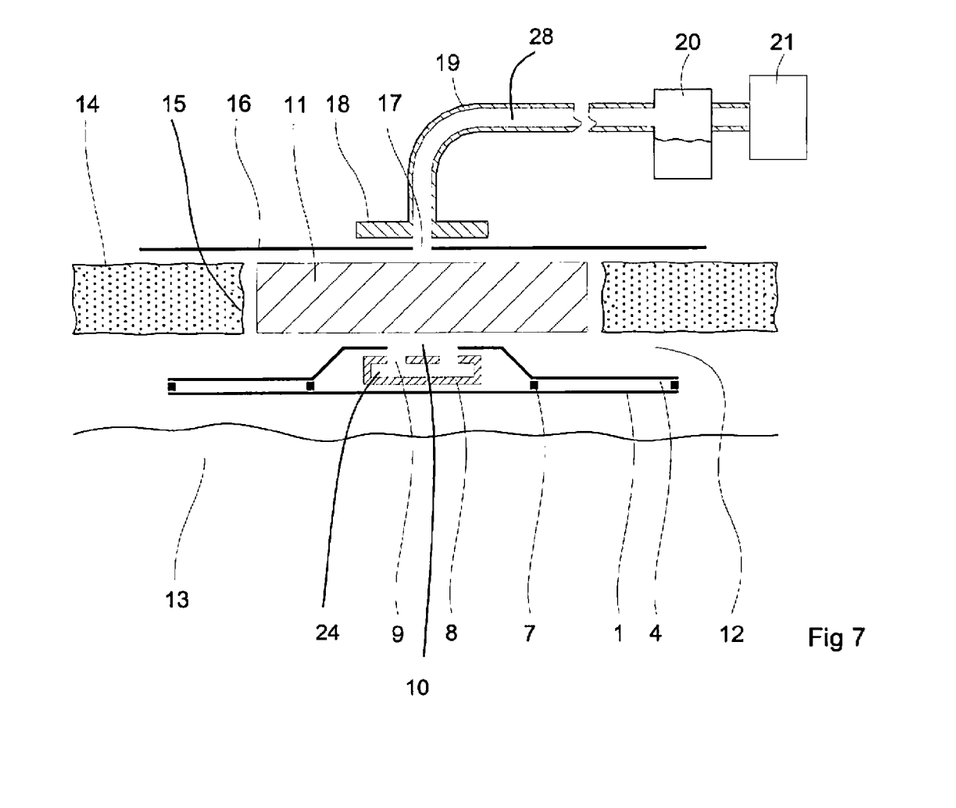
FIG. 7 shows a particularly preferred embodiment of a negative-pressure dressing applied to a wound as a transverse section.

FIG. 7 shows a diagram of the use of a preferred embodiment of the wound dressing according to the invention during treatment of an abdominal wound. The wound dressing is applied to the floor of the wound (13), for example to the omentum majus or exposed inner organs. The peripheral area of the wound dressing is located in the space (12) between the floor of the wound (13) and the abdominal wall (14). As per the embodiment shown in FIG. 7, the wound dressing comprises a liquid-permeable layer (11) which preferably comprises a porous polymer foam. With respect to its size, the fluid-permeable layer (11) ought to be provided such that it is in contact with the wound edges (15). This is advantageous particularly when using a porous polymer foam as a liquid-permeable layer (11), since it is known that contact of the wound edge (15) with a porous polymer foam promotes the growth of wound edge tissue. The wound and the wound surroundings are covered by an air-impermeable covering film (16). The covering film (16) preferably has an adhesive layer (not shown) on part of or over the entire surface of the side pointing toward the wound, so that it can be adhered firmly to the skin area surrounding the wound. Furthermore, at least one opening (17) is introduced in the central area of the covering film (16) to enable fluid transport. A negative-pressure connector (18) is fastened over the region of the opening (17). The negative-pressure connector (18) is connected to a canister (20) and a negative-pressure source (21) via the negative-pressure line (19).

In the context of the present invention, particularly suitable portable negative-pressure units which comprise canister (20) and negative-pressure source (21) separably in a single unit are described in the German patent applications having application numbers DE102009038130.9 and DE102009038131.7. With respect to suitable negative-pressure connectors (18), reference is made to the already mentioned German patent applications having application numbers DE 10 2010 003 273.1, DE 10 2010 003 272.3 and DE 10 2009 060 596.7.

Producing the Wound Dressing:

The invention further relates to a process for producing a wound dressing for negative-pressure therapy, where the wound dressing is intended particularly for treating abdominal wounds, comprising the steps of a) providing a first flexible film (1) having a first side and a second side, wherein the first side is intended for application onto the floor of the wound (13), more particularly onto exposed inner organs or onto the omentum majus, and wherein the film has a multiplicity of openings (5, 6) distributed over the surface, b) providing a conduit (2) consisting of a pliable elastomeric material having a thickness (H) of not more than 30 mm, wherein the conduit has at least one continuous hollow space (3), and wherein the conduit (2) has in addition a multiplicity of openings, c) applying the conduit (2) to the second side of the first film (1).

According to a preferred embodiment, the process can comprise the further step of a) applying a second film (4) to the combination of first film (1) and conduit (2).

According to a further preferred embodiment, the conduit (2) from step b) is made of a material which has a Shore A hardness of not more than 60, preferably less than 50, more particularly less than 45, particularly preferably less than 40.

According to a particularly preferred embodiment, the invention additionally relates to a process for producing a wound covering which comprises a combination of at least three radially arranged conduits (2) and one conduit plate (8). In practice, it proves advantageous to first produce the combination of the at least three conduits (2) and one conduit plate (8), and to then apply the combination to the first flexible film (1). According to this particularly preferred embodiment, the process comprises the steps of:

a) providing a first flexible film (1) having a first side and a second side, wherein the first side is intended for application onto the floor of the wound (13), more particularly onto exposed inner organs or onto the omentum majus, and wherein the film (1) has a multiplicity of openings (5, 6) distributed over the surface, b) providing a combination of at least three conduits (2) having a conduit plate (8), wherein the conduit (2) comprises a pliable elastomeric material having a thickness (H) of not more than 30 mm, and wherein the conduits (2) have in addition at least one continuous hollow space (3) and a multiplicity of openings (22), c) applying the combination of conduits (2) and conduit plate (8) to the second side of the first film (1).

According to a further particularly preferred embodiment, the process can comprise the further step of a) applying a second film (4) to the combination of first film (1), conduits (2) and conduit plate (8), wherein the second film is applied to the side of the combination pointing away from the wound during use.

According to a further embodiment which is particularly advantageous for the practical use of the wound dressing in negative-pressure therapy, the conduit (2) from step b) is made of a material which has a Shore A hardness of not more than 60, preferably less than 50, more particularly less than 45, particularly preferably less than 40.

Use:

In the case of use for negative-pressure therapy of large-area wounds in the abdominal region, the wound dressing according to the invention is first laid onto the floor of the wound (13). The edge areas of the wound dressing can then be inserted between the abdominal wall (14) and floor of the wound (13) over a depth of about 1 to 15 cm in order to achieve planar covering of the floor of the wound (13). Optionally provided pockets (25) open toward the middle of the wound dressing can facilitate the insertion of the edge area of the wound dressing between the abdominal wall and floor of the wound, by the treating physician inserting an abdominal or intestinal spatula into the pockets and then introducing the edge area of the wound dressing between the abdominal wall and the floor of the wound.

Advantageously, the wound dressing comprises one or more liquid-permeable layers (11). The one or more liquid-permeable layers can comprise a porous polymer foam material. It is very beneficial for wound healing when the liquid-permeable layer (11) is adjusted to the shape of the wound such that the wound edges (15) are in complete contact with the one or more liquid-permeable layers (11).

For air-tight closure of the wound region, an air-impermeable covering material (16) is laid over the wound. The edges of the covering material (16) are adhesively bonded onto the intact skin. In addition, a negative-pressure connecting piece (18) is attached in order to establish a functional connection of the wound space to a negative-pressure source (21) located outside the covering material (16), for example a negative-pressure pump, so that negative pressure can be established in the wound space and liquids can be sucked off from the wound space. The negative-pressure connecting piece (18) is preferably adhesively bonded onto the exterior side of the covering material (16) facing away from the wound, and prior to adhesion, a suitable opening (17) is cut into the otherwise air-impermeable covering material (16). Negative-pressure therapy is initiated by connecting the negative-pressure connecting piece (18) to a negative-pressure source (21) and applying constant negative pressure, or negative pressure which varies over time, for a period of a few minutes up to two or more days.

"Constant negative pressure" is understood here to mean that negative pressure is held largely constant during treatment. "Largely constant" means that negligible changes in negative pressure, for example by +/−15%, can occur during treatment.

A preferred constant negative pressure is the range from at least 80 mmHg up to no more than 250 mmHg, preferably 125 mmHg.

"Negative pressure which varies over time" is understood here to mean that negative pressure is specifically varied during treatment. Specific variation in air pressure is understood to mean those variations in air pressure which begin when a first desired value for negative pressure has been achieved after application of the negative-pressure bandage. By contrast, the first rising phase of negative pressure, which occurs after applying the bandage until the first desired value is reached, is not comprised by the term "negative pressure which varies over time". This applies in the same way to the lowering of negative pressure to ambient air pressure, which is necessary at the end of treatment and which is likewise not comprised by the term "negative pressure which varies over time".

"Negative pressure which varies over time" is delimited by a minimum corresponding to ambient air pressure and by a maximum corresponding to a maximum negative pressure of 250 mmHg, preferably 150 mmHg, more particularly 125 mmHg. The actual negative pressure applied during treatment shifts within this range defined by its threshold values. "Negative pressure which varies over time" thus comprises, for example, a single or repeated change between one or more higher negative-pressure values and one or more lower negative-pressure values. Similarly, "negative pressure which varies over time" comprises a specific single or repeated change between ambient pressure and one or more higher negative-pressure values which is taking place during treatment.

In a preferred embodiment, the maximum negative pressure for negative pressure which varies over time is 125 mmHg. In this embodiment, the lower limit for the variation in negative pressure is ambient air pressure. During treatment, negative pressure varies between or within these threshold values.

In a further preferred embodiment, the maximum negative pressure for negative pressure which varies over time is 125 mmHg. In this embodiment, the lower limit for the variation in negative pressure is 20 mmHg. During treatment, the negative pressure varies between or within these threshold values.

For the two abovementioned embodiments, the change between the upper pressure value and the lower pressure value can occur periodically or nonperiodically. A periodical change is preferred. The time intervals in which the higher negative pressure is held and in which the lower negative pressure or ambient pressure is held can each differ in length. Preferably, a lower negative pressure is held for longer than a higher negative pressure. Suitable time intervals in which in each case a particular negative-pressure setting or ambient pressure is held are, for example, 1 min, 2 min, 5 min, 10 min, 30 min, 1 h, 12 h or 24 h.

Particular preference is given to a varying negative pressure having the parameters mentioned below, providing, during treatment, a continuous change between the two negative-pressure values in the intervals specified:

a negative pressure of 125 mmHg over 2 min, followed by a negative pressure of 20 mmHg over 5 min.

Accordingly, the present invention describes a process for negative-pressure wound therapy, more particularly for a wound in the abdominal region, comprising the steps of a) laying a combination of first film and conduit or a combination of first film, conduit and conduit plate or a combination of first film, conduit and second film or a combination of first film, conduit, conduit plate and second film onto the wound, b) optionally applying one or more liquid-permeable layers (11) to the first film or second film, c) sealing the wound using a suitable air-tight covering (16), d) attaching a negative-pressure connector (18), e) applying negative pressure for at least 30 minutes and for not more than 5 days.

What is claimed is:

1. A wound dressing for use in negative-pressure wound therapy for treating abdominal wounds, comprising:
    a first flexible film (1) having a first side and a second side, where the first side is intended for application onto the floor of the wound (13), onto exposed inner organs or onto the omentum majus, wherein
    the wound dressing comprises at least one conduit (2) which is applied to the second side of the first film (1), said conduit (2) being fabricated from a pliable elastomeric material having a thickness (H) of not more than 30 mm,
    where the conduit (2) is planar and is indissolubly and extensively bound to the second side of the first film (1) and comprises walls which define at least one continuous substantially rectangular hollow space (3) wherein the conduit (2) has a substantially rectangular cross section in which at least 90% of an area of a bottom surface of the conduit (2) projected perpendicularly onto the first film is indissolubly bound to the second side of the first film (1), said conduit (2) having a width and a length wherein the width is substantially uniform along substantially the entire length,
    where both the conduit (2) and the first film (1) have a multiplicity of openings, so that a fluid connection can be established between the conduit (2) and the wound space, wherein at least some of openings (5) in the first film (I) and openings (22) in the conduit (2) overlap and are aligned with each other,
    where there is a fluid-conducting connection between the conduit (2) and a negative-pressure source (21) by means of at least one terminal opening (23), and
    where the wound dressing on the side facing away from the wound during use has at least one or more pockets (25) which are on the periphery and open toward the middle of the wound dressing and which have a depth of not more than 6 cm, and which facilitate uniform application and laying out the wound dressing onto the floor of the wound (13), wherein the pockets (25) each are formed by folding the first flexible film (1) or the combination of the first film (1) and a second film (4) and/or by applying further film pieces.

2. The wound dressing according to claim 1, wherein the conduit (2) is made of a material which has a Shore A hardness of not more than 60.

3. The wound dressing according to claim 1, wherein the conduit (2) is a drainage tube for medical purposes, and wherein the drainage tube comprises a polymer selected from the group consisting of NJ, PVC, PE, PET, PTFE, silicone and mixtures thereof.

4. The wound dressing according to claim 1, wherein the openings are holes and wherein the sum of the open areas of the holes of the first film (1) is at least 0.1% and not more than 20% of the areal extent of the film.

5. The wound dressing according to claim 1, wherein at least three conduits (2) are applied to the second side of the first film (1), and wherein the conduits (2) are applied in a radial arrangement or in a parallel arrangement.

6. The wound dressing according to claim 1, further comprising a second flexible film (4), wherein the second film (4) is applied to the side of the combination of first film (1) and conduit (2) facing away from the wound during use.

7. The wound dressing according to claim 6, wherein the second film (4) has a multiplicity of openings distributed over the surface which are suitable for conducting fluid.

8. The wound dressing according to claim 7, wherein the openings (5, 6) present in the first film (1) and the openings present in the second film are arranged such that the openings do not substantially overlap with one another.

9. The wound dressing according to claim 6, wherein the second film is substantially fluid impermeable and has only a single opening (10) arranged in the central area.

10. The wound dressing according to claim 1, wherein the first flexible film (1) and/or—if present—the second flexible film (4) is a thermoplastic film for medical purposes selected from the group consisting of PU, PE, PET, PVC, silicone and mixtures thereof.

11. The wound dressing according to claim 6, wherein the second flexible film (4)
a) is indissolubly bound, at least in places, to the at least one conduit (2), and/or
b) is indissolubly bound, at least in places, to the first flexible film (1).

12. The wound dressing according claim 1, further comprising a conduit plate (8) which is applied to the second side of the first flexible film (1) and is fastened at one or both of two ends of the at least one conduit (2).

13. The wound dressing according to claim 12, wherein the conduit plate (8) is in the form of a planar socket having an inner hollow space (24), and wherein, in addition, the end(s) of the at least one conduit (2) can be introduced such that a fluid connection can be established between the lumina (3) of the conduit (2) and the hollow space of the conduit plate (24).

14. The wound dressing according to claim 1, further comprising one or more liquid-permeable layers (11) for application onto the side of the wound dressing facing away from the wound during use.

15. The wound dressing according to claim 14, wherein the liquid-permeable layer (11) comprises a porous polymer foam material selected from the group consisting of PU, PVA and silicone.

16. The wound dressing according to claim 1, further comprising an air-impermeable covering material (16) for air-tight closure of the wound and of the wound surroundings, wherein the covering material (16) has an adhesive edge.

17. The wound dressing according to claim 16, further comprising a device (18) applied to the air-impermeable covering material (16) on the side facing away from the wound, said device being a negative-pressure connecting piece (port) for functional connection of the wound space to a negative-pressure source (21) located outside the covering material (16), so that negative pressure is established in the wound space and liquids are sucked off from the wound space.

18. A ready-to-use set for negative-pressure wound treatment, more particularly for treating abdominal wounds, comprising:
a) a wound dressing according to claim 1;
b) at least one liquid-permeable layer (11) for application onto the side of the wound dressing facing away from the wound during use, wherein the at least one liquid-permeable layer (11) comprises one or more flat pads consisting of a porous polymer foam material selected from the group consisting of PU, PVA and silicone;
c) an air-impermeable covering material (16) for air-tight closure of the wound and of the wound surroundings, wherein the covering material (16) has an adhesive edge; and
d) a negative-pressure connector (18) for functional connection of the wound space to a negative-pressure source (21) located outside the covering material, so that negative pressure is established in the wound space and liquids are sucked off from the wound space, wherein the negative-pressure connector (18) is intended for attachment onto the external side of the covering material facing away from the wound during use;
and wherein all of components a) to d) are each individually sterile packed.

19. A process for producing a wound dressing according to claim 1, comprising the steps of:
a) providing a first flexible film (1) having a first side and a second side, wherein the first side is intended for application onto the floor of the wound (13) onto exposed inner organs or onto the omentum majus, and wherein the film (1) has a multiplicity of openings (6) distributed over the surface;
b) providing at least one conduit (2) consisting of a pliable elastomeric material having a Shore A hardness of not more than 60 and a thickness (H) of not more than 30 mm, wherein the conduit (2) has at least one continuous hollow space (lumen) (3), and wherein the at least one conduit (2) has in addition a multiplicity of openings (22); and,
c) applying the at least one conduit (2) to the second side of the first film (1).

20. A process for producing a wound dressing according to claim 6, comprising the steps of:
a) providing a first flexible film (1) having a first side and a second side, wherein the first side is intended for application onto the floor of the wound (13) onto exposed inner organs or omentum majus, and wherein the film (1) has a multiplicity of openings (5, 6) distributed over the surface;
b) providing a combination of at least three conduit elements (2) which are connected by a conduit plate (8), wherein the conduits (2) consist of a pliable elastomeric material having a Shore A hardness of not more than 60 and a thickness (H) of not more than 30 mm, and wherein the conduit (2) has at least one continuous hollow space (3), and wherein the conduit has in addition a multiplicity of openings (22);
c) applying the combination of conduits (2) and conduit plate (8) to the first film (1); and,
d) applying a second flexible film (4) to the combination of first it (1), conduits (2) and conduit plate (8), wherein the second film is applied to the side of the combination pointing away from the wound during use.

* * * * *